US012728107B2

(12) United States Patent
Noda et al.

(10) Patent No.: US 12,728,107 B2
(45) Date of Patent: Sep. 8, 2026

(54) SIRTUIN ACTIVATOR, AND METHOD FOR ACTIVATING SIRTUIN

(71) Applicants: Yuki Gosei Kogyo Co., Ltd., Tokyo (JP); Kyushu University, National University Corporation, Fukuoka (JP)

(72) Inventors: Tetsuji Noda, Tokyo (JP); Tomotsune Onaga, Tokyo (JP); Yoshinori Katakura, Fukuoka (JP)

(73) Assignees: Yuki Gosei Kogyo Co., Ltd., Tokyo (JP); Kyushu University, National University Corporation, Fukuoka (JP)

( * ) Notice: Subject to any disclaimer, the term of this patent is extended or adjusted under 35 U.S.C. 154(b) by 673 days.

(21) Appl. No.: 18/041,730

(22) PCT Filed: Aug. 18, 2021

(86) PCT No.: PCT/JP2021/030165

§ 371 (c)(1),
(2) Date: May 9, 2023

(87) PCT Pub. No.: WO2022/039190

PCT Pub. Date: Feb. 24, 2022

(65) Prior Publication Data

US 2023/0310355 A1 Oct. 5, 2023

(30) Foreign Application Priority Data

Aug. 18, 2020 (JP) ................................ 2020-138157

(51) Int. Cl.
*A61K 31/197* (2006.01)
*A61P 17/00* (2006.01)
*A61P 21/00* (2006.01)

(52) U.S. Cl.
CPC ............ *A61K 31/197* (2013.01); *A61P 17/00* (2018.01); *A61P 21/00* (2018.01)

(58) Field of Classification Search
CPC .................................................. A61K 31/197
See application file for complete search history.

(56) References Cited

U.S. PATENT DOCUMENTS

| | | | |
|---|---|---|---|
| 5,869,068 | A | 2/1999 | De Lacharriere et al. |
| 2006/0039935 | A1 | 2/2006 | Antosh et al. |
| 2009/0263367 | A1 | 10/2009 | Foley |

FOREIGN PATENT DOCUMENTS

| | | | |
|---|---|---|---|
| JP | 899862 | A | 4/1996 |
| JP | 201157580 | A | 3/2011 |
| JP | 201179797 | A | 4/2011 |
| JP | 201597508 | A | 5/2015 |
| WO | 2020160619 | A1 | 8/2020 |

OTHER PUBLICATIONS

BulkSupplement beta alanine powder.*
Budczies et al. Journal of Proteomics, 2013, 94: 279-288, 2013.*
Huang et al. Oncology Reports, 2016, 35(5):2801-2810.*
Kamei et al., CAS: 2020:1726712, 2020.*
Del Favero et al., “Beta-Alanine (Carnosyn TM) Supplementation in Elderly Subjects (60-80 years): Effects on Muscle Carnosine Content and Physical Capacity”, Amino Acids, vol. 43, pp. 49-56. 2012.
Furst et al., “ß-Alanine Supplementation Increased Physical Performance and Improved Executive Function Following Endurance Exercise in Middle Aged Individuals”, Journal of the International Society of Sports Nutrition, vol. 15, No. 32, pp. 1-8. 2018.
Howitz et al., “Small Molecule Activators of Sirtuins Extend *Saccharomyces cerevisiae* Lifespan”, Nature, vol. 425, p. 191-196. Sep. 11, 2003 (Japanese).
International Search Report and Written Opinion in PCT/JP2021/030165, 13 pages, with partial translation. Sep. 21, 2021.
“Overseas Topics of Food Processing”, Food Processing, CMP Japan Co., Ltd., vol. 44, No. 6, pp. 77-83. 2009.
Pence et al., “Effects of Exercise and Dietary Epigallocatechin Gallate and ß-Alanine on Skeletal Muscle in Aged Mice”, Appl. Physiol. Nutr. Metab., vol. 41, pp. 181-190. 2016.
Stout et al., The Effect of Beta-Alanine Supplementation on Neuromuscular Fatigue in Elderly (55-92 years): a Double-Blind Randomized Study, Journal of the International Society of Sports Nutrition, vol. 5, No. 21, pp. 1-6. 2008.
Supplementary European Search Report in European Application No. 21 85 8334, 8 pages. Oct. 4, 2024.
Kyriazis, “Anti-Ageing Potential of Carnosine: Approaches Toward Sucessful Ageing”, Drug Discovery Today: Therapeutic Strategies Aging, vol. 7, No. 3-4, pp. 45-49. 2010.
Edwards et al., “Mechanisms of Amino Acid-Mediated Lifespan Extension in Caenorhabditis Elegans”, BMC Genetics, vol. 16, No. 8, 24 pages. 2015.
Lavu et al., “Sirtuins—Novel Therapeutic Targets to Treat Age-Associated Diseases”, Nature Reviews Drug Discovery, vol. 7, pp. 841-853. Oct. 2008.
Song et al., “Distinctive Roles of Sirtuins on Diabetes, Proctective or Detrimental?” Frontiers in Endocrinology, vol. 9, article 724, 13 pages. Nov. 29, 2018.

* cited by examiner

*Primary Examiner* — Rei Tsang Shiao
(74) *Attorney, Agent, or Firm* — Heslin Rothenberg Farley & Mesiti P.C.

(57) ABSTRACT

The object of the present invention is to provide an inexpensive and effective sirtuin activator derived from natural products.
The problem can be solved by a sirtuin activator comprising β-alanine or a salt thereof, or a composition for activating sirtuin comprising the sirtuin activator as an active ingredient, of the present invention.

11 Claims, 2 Drawing Sheets

Specification includes a Sequence Listing.

[Figure 1]
(A)
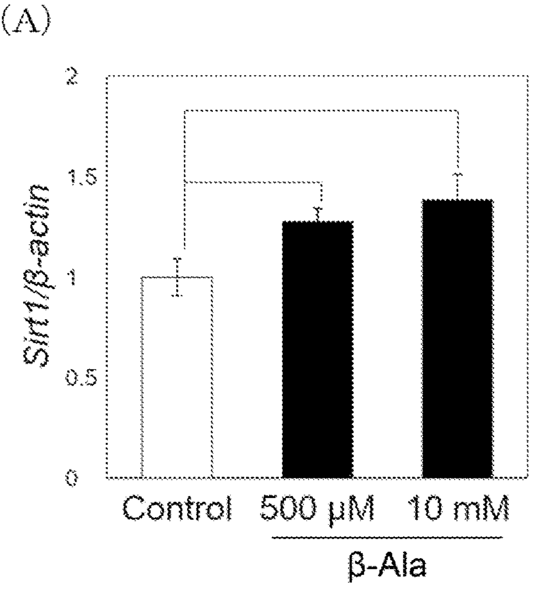
(B)
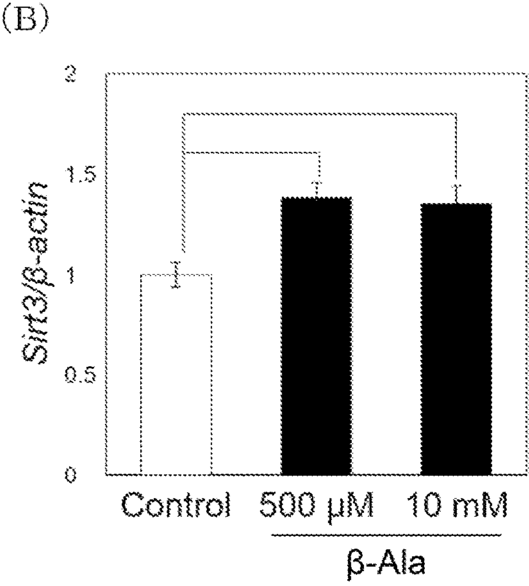
[Figure 2]
(A)
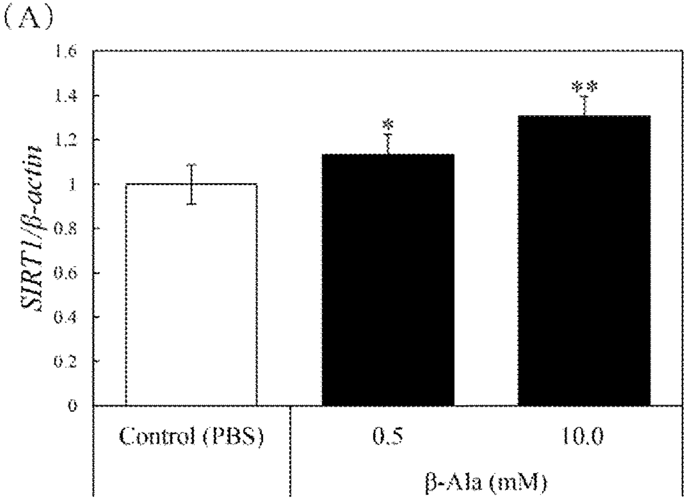
(B)
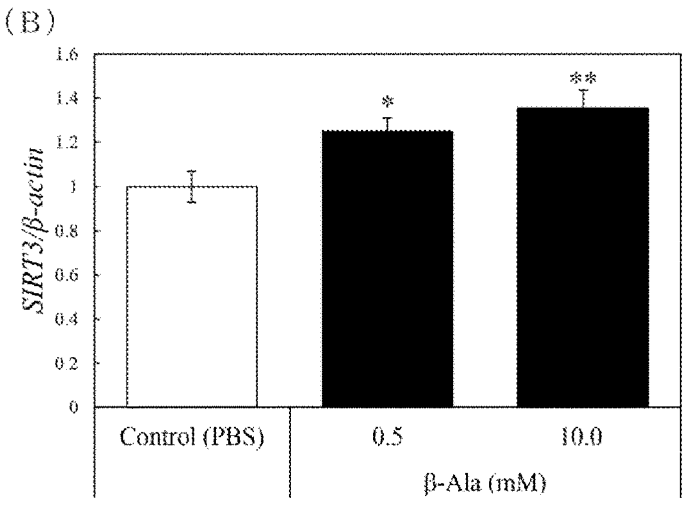

[Figure 3]
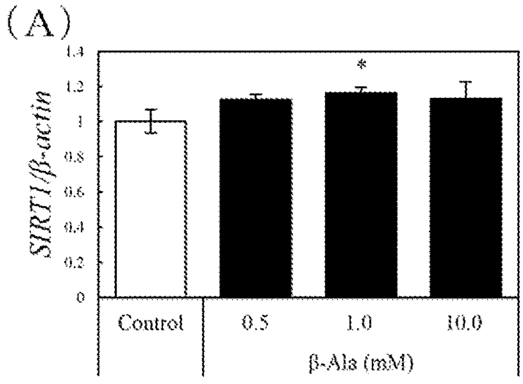
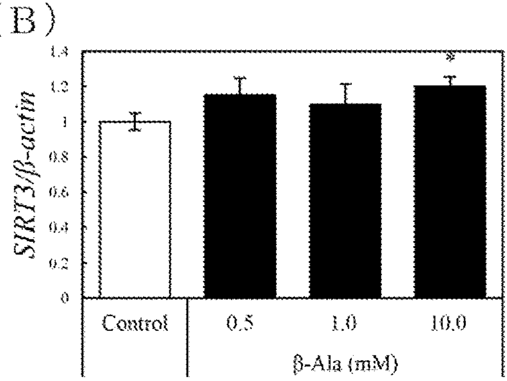
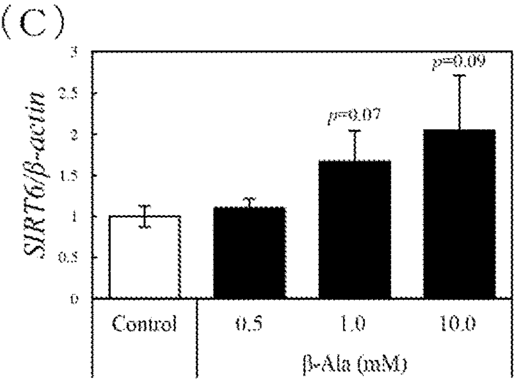
[Figure 4]
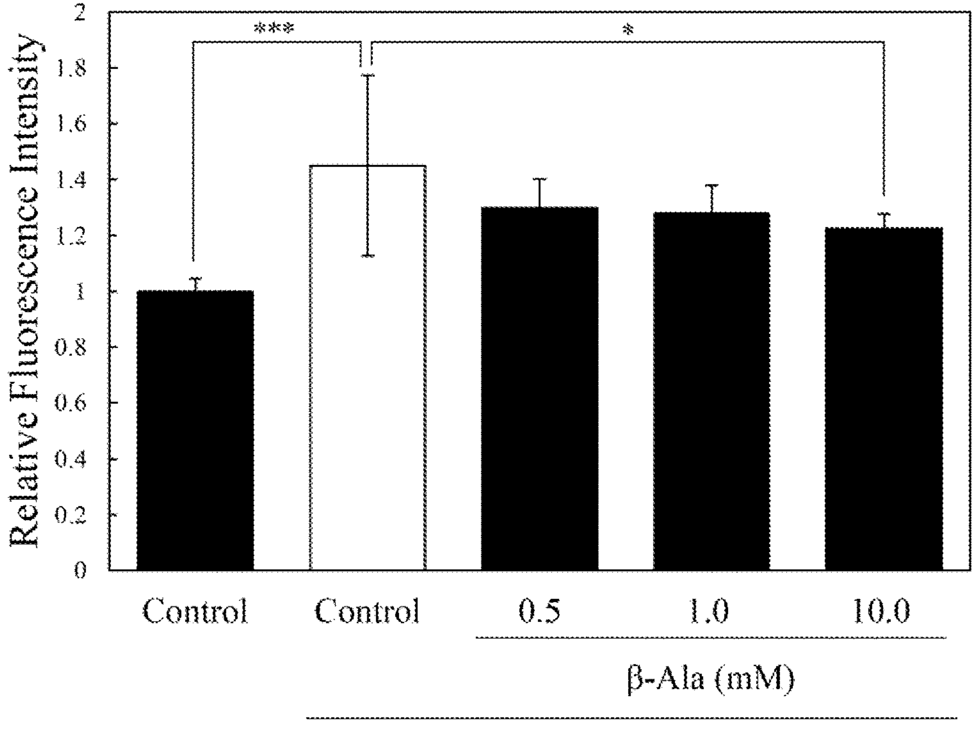

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: beta-actin  forward primer

<400> SEQUENCE: 1

ggccaggtca tcactattg                                                    19


<210> SEQ ID NO 2
<211> LENGTH: 21
<212> TYPE: DNA
<213> ORGANISM: Artificial Sequence
<220> FEATURE:
<223> OTHER INFORMATION: beta-actin  reverse primer

<400> SEQUENCE: 2

gaggtcttta cggatgtcaa c                                                 21


<210> SEQ ID NO 3
<211> LENGTH: 24
<212> TYPE: DNA
<213> ORGANISM: Artificial Sequence
<220> FEATURE:
<223> OTHER INFORMATION: Sirt1 forward primer

<400> SEQUENCE: 3

gcagacgtgg taatgtccaa acag                                              24


<210> SEQ ID NO 4
<211> LENGTH: 25
<212> TYPE: DNA
<213> ORGANISM: Artificial Sequence
<220> FEATURE:
<223> OTHER INFORMATION: Sirt1 reverse primer

<400> SEQUENCE: 4

acatcttggc agtatttgtg gtgaa                                             25


<210> SEQ ID NO 5
<211> LENGTH: 21
```

<212> TYPE: DNA
<213> ORGANISM: Artificial Sequence
<220> FEATURE:
<223> OTHER INFORMATION: Sirt3 forward primer

<400> SEQUENCE: 5
atgcacggtc tgtcgaaggt c 21

<210> SEQ ID NO 6
<211> LENGTH: 24
<212> TYPE: DNA
<213> ORGANISM: Artificial Sequence
<220> FEATURE:
<223> OTHER INFORMATION: Sirt3 reverse primer

<400> SEQUENCE: 6
agaacacaat gtcgggtttc acaa 24

<210> SEQ ID NO 7
<211> LENGTH: 24
<212> TYPE: DNA
<213> ORGANISM: Artificial Sequence
<220> FEATURE:
<223> OTHER INFORMATION: Human Sirt1 forward

<400> SEQUENCE: 7
gcctcacatg caagctctag tgac 24

<210> SEQ ID NO 8
<211> LENGTH: 24
<212> TYPE: DNA
<213> ORGANISM: Artificial Sequence
<220> FEATURE:
<223> OTHER INFORMATION: Human Sirt1 reverse

<400> SEQUENCE: 8
ttcgaggatc tgtgccaatc ataa 24

<210> SEQ ID NO 9
<211> LENGTH: 24
<212> TYPE: DNA
<213> ORGANISM: Artificial Sequence
<220> FEATURE:
<223> OTHER INFORMATION: Human Sirt3 forward

<400> SEQUENCE: 9
agccctcttc atgttccgaa gtgt 24

<210> SEQ ID NO 10
<211> LENGTH: 24
<212> TYPE: DNA
<213> ORGANISM: Artificial Sequence
<220> FEATURE:
<223> OTHER INFORMATION: Human Sirt3 reverse

<400> SEQUENCE: 10
tcatgtcaac acctgcagtc cctt 24

<210> SEQ ID NO 11
<211> LENGTH: 17
<212> TYPE: DNA
<213> ORGANISM: Artificial Sequence
<220> FEATURE:
<223> OTHER INFORMATION: Sirt6 forward

<400> SEQUENCE: 11

-continued

```
aattacgcgg cggggct                                                    17


<210> SEQ ID NO 12
<211> LENGTH: 17
<212> TYPE: DNA
<213> ORGANISM: Artificial Sequence
<220> FEATURE:
<223> OTHER INFORMATION: Sirt6 reverse

<400> SEQUENCE: 12

cgcgcgctct caaaggt                                                    17
```

SIRTUIN ACTIVATOR, AND METHOD FOR ACTIVATING SIRTUIN

CROSS REFERENCE TO RELATED APPLICATIONS

This application is a U.S. National Phase filing under 35 U.S.C. § 371 of International Application PCT/JP2021/030165, filed Aug. 18, 2021, and published as WO 2022/039190 A1 on Feb. 24, 2022. PCT/JP2021/030165 claims priority from Japanese application number 2020-138157, filed Aug. 18, 2020. The entire contents of each of these prior applications are hereby incorporated herein by reference.

SEQUENCE LISTING

The instant application contains an electronic sequence listing. The contents of the electronic sequence listing (ASCII; H2628355.txt; Size: 2,608 bytes; and Date of Creation: Mar. 22, 2023) is herein incorporated by reference in its entirety.

TECHNICAL FIELD

The present invention relates to a sirtuin activator and a method for activating sirtuin.

BACKGROUND ART

The Sir2 gene identified in yeast has been reported to shorten life span when defective and to extend life span when overexpressed. Therefore, the sirtuin genes are considered to be longevity genes or anti-aging genes. The sirtuin genes encode histone deacetylases, and seven sirtuin genss (Sirt1~7) have been reported in mammals.

Although the sirtuin genes are known to be activated by calorie restriction, studies are underway to increase the expression of sirtuins and extend life span by methods other than calorie restriction. Specifically, resveratrol, a polyphenol compound contained in wine, has been disclosed to activate sirtuins (Non-Patent literature 1). It is disclosed that Gnetin C (Patent literature 1) and ε-viniferin (Patent literature 2) have sirtuin activation.

CITATION LIST

Patent Literature

[Patent literature 1] JP 2011-079797 A
[Patent literature 2] JP 2011-057580 A

Non-Patent Literature

[Non-patent literature 1] Nature, 2003 (England) vol 425, p 191-196

SUMMARY OF INVENTION

Technical Problem

Inexpensive and effective sirtuin activators derived from natural products are expected.

Therefore, the object of the present invention is to provide an inexpensive and effective sirtuin activator derived from natural products.

Solution to Problem

The present inventors have conducted intensive studies into an inexpensive and effective sirtuin activator derived from natural products, and as a result, surprisingly, found that β-alanine or salt thereof activates sirtuin.

The present invention is based on the above findings.

Accordingly, the present invention relates to:

[1] a sirtuin activator comprising β-alanine or a salt thereof,

[2] a composition for activating sirtuin, comprising the sirtuin activator of item [1], as an active ingredient,

[3] a composition for activating sirtuin of item [2], for extending life span or inhibiting aging

[4] the composition for activating sirtuin of item [2], wherein the sirtuin is activated by promoting glycometabolism, improving insulin resistance, promoting insulin secretion, promoting cholesterol metabolism, promoting fatty acid metabolism, protecting neuron cell, arresting cell cycle, inducing oxidative stress resistance, inducing cell death suppression, maintaining and regulating circadian rhythm, or suppressing inflammation,

[5] the composition for activating sirtuin of item [2], for preventing or treating type 2 diabetes mellitus, for preventing or treating metabolic disease, for preventing or treating cancer, for preventing or treating neurological disease, for preventing or treating cardiovascular disease, for preventing or treating chronic obstructive pulmonary disease, for preventing or treating osteoporosis, for preventing or treating immune disease, or for preventing or treating disuse atrophy,

[6] the composition for activating sirtuin of item [5], wherein the metabolic disease is metabolic syndrome,

[7] the composition for activating sirtuin of item [5], wherein the cancer is colorectal cancer, skin cancer, or breast cancer,

[8] the composition for activating sirtuin of item [5], wherein the neurological disease is Alzheimer's disease, or amyotrophic lateral sclerosis,

[9] the composition for activating sirtuin of item [5], wherein the cardiovascular disease is arteriosclerosis,

[10] the composition for activating sirtuin of item [5], wherein the immune disease is atopic dermatitis, hay fever, or rheumatoid arthritis,

[11] the composition for activating sirtuin of any one of the items [2] to [10], wherein the composition is food composition, and

[12] a method for activating sirtuin, comprising step of letting an effective amount of the sirtuin activator according to claim 1 or the composition for activating sirtuin of any one of the items [2] to [11], ingest a subject (excluding medical treatment for human).

The present specification discloses:

[13] a muscle cell activator comprising β-alanine or salt thereof,

[14] the muscle cell activator of the item [13], wherein the activation of muscle cells is a promotion of secretion of myokine from muscle cells,

[15] the muscle cell activator of the item [13] or [14], wherein the myokine is a substance that activates sirtuin or inhibits aging,

[16] the muscle cell activator of the items [13] to [15], wherein the inhibition of aging is a decrease in an activity of β-galactosidase that relates aging, and

[17] a composition for activating muscle cells, comprising the muscle cell activator of the items [13] to [16], as an active ingredient.

Advantageous Effects of Invention

According to the sirtuin activator of the present invention, sirtuins can be efficiently activated.

BRIEF DESCRIPTION OF THE DRAWINGS

FIG. 1 is graphs showing the expression (transcription) of Sirt1 gene (A) or Sirt3 gene (B) when mouse skeletal muscle-derived myoblast cell line C2C12 cells differentiated into myotube cells, are treated with β-alanine.

FIG. 2 is graphs showing expressions (transcriptions) of Sirt1 gene (A) or Sirt3 gene (B) when HaCaT cells, a human epidermal keratinocyte cell line, are treated with β-alanine.

FIG. 3 is graphs showing expressions of Sirt1 gene (A), Sirt3 gene (B), and Sirt6 (C) of dermal cells when substances secreted from muscle cells (C2C12 cells) by β-alanine are added thereto.

FIG. 4 is a graph showing expressions of β-galactosidase that relates aging of dermal cells when substances (culture supernatant) secreted from muscle cells (C2C12 cells) by β-alanine are added thereto.

DESCRIPTION OF EMBODIMENTS

[1] Sirtuin Activator

The sirtuin activator of the present invention comprises β-alanine or salt thereof. The sirtuin activator of the present invention may also comprise other amino acid having a carboxyl group and an amino group, or salt thereof, or the like. The sirtuin activator may comprise β-alanine or salt thereof, or other amino acid having a carboxyl group and an amino group, or its salt, or a combination of two or more of them.

β-alanine is represented by the following formula [1]:

[Chem. 1]

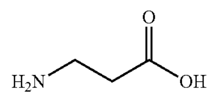

[1]

and is also called 3-aminopropanoic acid. Extracts, concentrates, or purified products from foods or natural products that contain relatively large amounts of β-alanine, can be used, as β-alanine comprised in the sirtuin activator of the present invention. In addition, synthetic β-alanine may be used. For example, β-alanine can be synthesized from β-propiolactone by the β-alanine synthesis method (Ford, Org. Sys. Coll. Vol. 3, 34(1955)). As another synthetic method, it can be synthesized from acrylonitrile and ammonia.

The salt of β-alanine is not limited, so long as it is a salt with an inorganic base or an organic base, or a salt with an acid, and is a salt acceptable for medicine or food. Specific examples of the salt with the inorganic base or the organic base include a salt with an inorganic base, an organic base, or a metallic alkoxide. They can be prepared by mixing β-alanine with an inorganic base, an organic base, or a metallic alkoxide.

As the inorganic bases that can form salts, there may be mentioned a hydroxide, carbonate, hydrogen carbonate, acetate, or hydride of alkali metals (such as lithium, sodium, potassium, or the like); a hydroxide, hydride, or the like of alkaline earth metals (such as magnesium, calcium, or barium). As the organic bases that can form salts, there may be mentioned dimethylamine, triethylamine, piperazine, pyrrolidine, piperidine, 2-phenylethylamine, benzylamine, ethanolamine, diethanolamine, pyridine, collidine, or the like. Further, as the metallic alkoxide, there may be mentioned sodium methoxide, potassium tert-butoxide, magnesium methoxide, or the like. The salt of β-alanine is preferably a sodium salt, potassium salt, calcium salt, or a combination thereof.

Specific examples of the salt with an acid include a salt with an inorganic acid or an organic acid. As the inorganic acid that can form a salt, there may be mentioned hydrochloric acid.

Further, as the sirtuin activator, other amino acids having a carboxyl group and an amino group can also be used, in addition to β-alanine in the present invention. Specifically, there may be mentioned amino acids that make up proteins such as glycine, valine, leucine, isoleucine, alanine, arginine, glutamine, lysine, aspartic acid, glutamic acid, proline, threonine, histidine, phenylalanine, tyrosine, tryptophan, asparagine, serine and the like; and further free amino acids in the living body such as phosphoserine, phosphoethanolamine, hydroxyproline, sarcosine, and α-aminoadipic acid citrullin, α-amino-n-butyric acid, β-aminoisobutyric acid, γ-aminobutyric acid, 3-methylhistidine, 1-methylhistidine, carnosine, anserine, hydroxylysine, ornithine, ethanolamine, carnitine, and the like, but it is not particularly limited thereto.

In addition to β-alanine of the present invention, a derivative of β-alanine can also be used. In the present specification, the derivative of β-alanine means a compound in which a hydrogen atom bonded to methylene carbon in the main chain is substituted. Examples of the substituent include an alkyl group having 1 to 3 carbon atoms.

<<Sirtuin>>

Seven homologs of mammalian sirtuins, i.e. Sirt1 to Sirt7, have been reported. In yeast, a kind of microorganism, five homologs of sirtuins such as Sir2 have been reported. The sirtuins activated by the sirtuin activator of the present invention are not limited, as long as the sirtuins are deacetylases or their homologs, but include, for example, sirtuins derived from mammals, sirtuins derived from avian, sirtuins derived from fish, sirtuins derived from reptiles, sirtuins derived from amphibians, sirtuins derived from molluscs, sirtuins derived from insects, sirtuins derived from fungi, sirtuins derived from nematodes, sirtuins derived from arthropods, or sirtuins from protozoa. Sirtuins derived from mammals are preferable. As sirtuins of mammalian origin, there may be mentioned Sirt1, Sirt2, Sirt3, Sirt4, Sirt5, Sirt6, or Sirt7, and Sirt1, Sirt3, or Sirt6 is preferrable. Sirt1 is involved in mitochondrial biosynthesis, and Sirt3 is involved in the biosynthesis of enzymes involved in the removal of reactive oxygen species in mitochondria. Sirt6 is a histone deacetylase and is involved in regulation of telomere maintenance and cellular senescence, DNA repair, transcriptional regulation, and the like.

The term "activation of sirtuins" herein includes activation of sirtuin genes (e.g., increased transcription) or activation of sirtuin proteins (e.g., increased expression). The sirtuin activators of the present invention can activate sirtuins in cells constituting a living body. The sirtuin activator can activate sirtuin in, for example, but not limited to, skeletal muscle cells, skin epidermal cells, skin dermal cells, liver cells, adipocytes, nerve cells or the like.

Sirtuins act as NAD-dependent histone deacetylases, and they remove acetyl groups from acetylated proteins, such as histones and p53 on transcription factors. In addition, sirtuins are involved in the prolongation of life span and inhibition of aging of organisms through the activation thereof. Specifically, sirtuins have been reported to be involved in the gene expression during aging, intracellular metabolism, energy consumption, control of basic biological responses such as inflammation and stress response pathways, recovery of neurotrophic factor gene dysfunction in the brain, and improvement of learning and memory abilities. In particular, SIRT1 activation is involved in the control of glycogenesis and glycolysis-related genes, fatty acid oxidation, cholesterol control, fatty acid mobilization, adipokine control, suppression of insulin resistance, insulin secretion, neuronal protection, cell cycle arrest, induction of oxidative stress tolerance, induction of cell death inhibition, mediation of calorie restriction effects, maintenance and control of circadian rhythms, and suppression of inflammation. In addition, an activation of SITR3 exhibits functions such as mitochondrial protein deacetylation, control of acetate metabolism, fatty acid oxidation, and ATP production. Furthermore, sirtuins are effective in improving a variety of diseases, including, as a specific disease, type 2 diabetes, metabolic diseases (e.g., metabolic syndrome), cancer (e.g., colorectal cancer, skin cancer, or breast cancer), neurological diseases (e.g., Alzheimer's disease or amyotrophic lateral sclerosis), cardiovascular diseases (e.g., arteriosclerosis), chronic obstructive pulmonary disease, osteoporosis, immune diseases (e.g., atopic dermatitis, hay fever, or rheumatoid arthritis), or disuse atrophy.

Therefore, the sirtuin activator of the present invention can be used for prevention or treatment of these diseases. Activation of SIRT1 generates the same situation as during caloric restriction. Therefore, SIRT1 has anti-aging or life extension effects. SIRT1 is involved in the insulin resistance and dysfunction of beta cell, which are the causes of type 2 diabetes, in liver, skeletal muscle, adipose tissue, and pancreatic beta cells. Activation of SIRT1 improves insulin resistance and may be effective in the treatment and prevention of type 2 diabetes. SIRT1 activation also reduces cholesterol, adipokines, and insulin, which may be effective in the prevention and treatment of metabolic diseases (e.g., metabolic syndrome). In mice overexpressing SIRT1, the size, growth, and number of adenomas of colorectal cancer are reduced to one fourth. In mice wherein SIRT1 is activated by a SIRT1 activator (resveratrol), chemical-induced skin cancer is suppressed. Furthermore, SIRT3-deficient fetal fibroblasts (MEFs) become cancerous, and SIRT3 knockout mice develop estrogen receptor/progesterone receptor-positive breast cancer. Therefore, activation of SIRT1 or SIRT3 may suppress cancer. Activation of SIRT1 prevents accumulation of Aβ amyloid and tauopathy (pathological changes caused by denaturation and aggregation of tau protein). SIRT1 is also required for neuronal protection against neuroaxonal Wallerian degeneration, and also shows protective effects against amyotrophic lateral sclerosis and Alzheimer's disease models. Thus, activation of SIRT1 activity is effective against a wide range of neurological diseases such as amyotrophic lateral sclerosis or Alzheimer's disease. Cardiovascular disease (CVD) depends on complex interactions between cholesterol biosynthesis, the immune system, and endothelial cell function, and SIRT1 acts in an inhibitory manner against cardiac disease and arteriosclerosis. For example, SIRT1 is highly expressed in endothelial cells and has functions such as increasing endothelial-type NOS (eNOS), decreasing cellular senescence of smooth muscle cells, inflammation in arteries, suppressing of reactive oxygen species, and promoting vascular growth. Therefore, activation of SIRT1 is effective for the treatment and prevention of cardiovascular diseases (CVD) by suppressing cellular senescence, inflammation, and reactive oxygen species. Chronic obstructive pulmonary disease (COPD) is considered to be caused by oxidative stress. Upon exposure to oxidative stress (CSE), cytoplasmic SIRT1 is translocated into the nucleus and protects cells, but chronic exposure to oxidative stress (CSE) inhibits the nuclear translocation of SIRT1. Therefore, activation of SIRT1 may be effective against chronic obstructive pulmonary disease (COPD). Treatment of a disuse model of osteoporosis with SIRT1 agonists protects against osteoporosis. Therefore, activation of SIRT1 may be effective in the treatment or prevention of osteoporosis.

It has been reported that SIRT6 knockout mice exhibit premature aging-like symptoms. Since SIRT6-deficient cells exhibit high sensitivity to DNA damage, their association with these symptoms is inferred. The discovery that SIRT6 is a histone deacetylase and that histone acetylation strongly correlates with chromatin activation has led to the identification of a number of biological functions of SIRT6. Specific deacetylation has been shown to be involved in DNA replication and repair.

Telomeres prevent that chromosome ends from are recognized as DNA damage and abnormal fusion of chromosome ends due to degradation and repair. Then, histone deacetylation by SIRT6 is thought to work to maintain and stabilize telomere structure. In addition, SIRT6 has been found to play an important role in transcriptional regulation.

For example, suppression of the expression of RELA, a subunit of NF-κB, which is an important factor involved in life phenomena such as senescence, inflammation, immunity, cell proliferation, and apoptosis, has been shown to prevent senescence-like symptoms and metabolic abnormalities in SIRT6 knockout mice, thus avoiding early mortality.

Recently, it has been suggested that the level of hyperacetylation caused by SIRT6 deficiency correlates with the progression of cancer, and is also associated with immune disorders and metabolic syndrome. This finding is expected to lead to the development of new and innovative drugs for the prevention and treatment of aging and diseases.

The formulation of the sirtuin activator of the present invention is not particularly limited. For example, oral agents, such as powders, subtle granules, granules, tablets, capsules, suspensions, emulsions, syrups, extracts, or balls; or parenteral agents, such as injections, liquid for external use, ointments, suppositories, creams for local administration, or eye-drops, there can be mentioned.

The above oral agent can be prepared in accordance with conventional methods, using excipients, such as gelatin, alginate sodium, starch, cornstarch, saccharose, lactose, glucose, mannitol, carboxymethyl-cellulose, dextrin, polyvinyl pyrrolidone, crystalline cellulose, soy lecithin, sucrose, fatty acid ester, talc, magnesium stearate, polyethylene glycol, magnesium silicate, silicic anhydride, or synthetic aluminum silicate; binders, disintegrators, surfactants, lubricants, flow accelerator, diluents, preservatives, colorants, flavors, corrigents, stabilizers, humectants, antiseptics, antioxidant, or the like.

Examples of the parenteral agents include injections. In a preparation of the injections, an aqueous solvent such as normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, can be optionally used, in addition to the active ingredient.

A dose of the sirtuin activator may be appropriately determined in accordance with, for example, age, sex, body weight, or degree of symptom of each patient, the type of each active ingredient, type of each disease, route of administration, or the like, and the determined dosage can be administered orally or parenterally. For example, in the case of an adult, the intake amount of the sirtuin activator of the present invention is preferably 0.01 to 100 mg/kg per day as β-alanine. The above administration method is an example, and other administration methods may be used. It is desirable that the administration method, dose, administration period, administration interval, and the like, of the sirtuin activator to humans are determined by a controlled clinical trial.

In addition, dosage form for administration of the sirtuin activator is not limited to a drug medicine. That is, it can be administered as a food and drink of various form, such as a functional food, a healthy food (including drink), or an animal food stuff.

As a method for preparing a sirtuin activator containing β-alanine, known pharmaceutical preparation methods can be used except that β-alanine is contained as an active ingredient.

The sirtuin activator of the present invention may contain other components. Examples of the other components include, for example, emulsifiers such as edible fats and oils, water, glycerin fatty acid ester, sucrose fatty acid ester, sorbitan fatty acid ester, propylene glycol fatty acid ester, glycerin organic acid fatty acid ester, polyglycerol fatty acid ester, calcium stearoyl lactylate, sodium stearoyl lactate, polyoxyethylene sorbitan fatty acid ester; thickening stabilizers such as locust bean gum, carrageenan, alginic acids, pectin, xanthan gum, crystalline cellulose, carboxymethyl cellulose, methyl cellulose, agar, glucomannan, gelatin, starch, or chemical starch; salty taste agents such as salt, or potassium chloride; acidulants such as acetic acid, lactic acid, or gluconic acid; sugars or sugar alcohols; sweeteners such as stevia or aspartame; colorants such as beta-carotene, caramel, or red koji pigment; antioxidants such as tocopherol or tea extract; food materials or food additives such as flavoring agent; pH adjuster; food preservative, or shelf life improver. Further, the sirtuin activator may contain various vitamins, or functional materials such as coenzyme Q, plant sterol, or milk fat globule membrane. The amount of these other components is preferably 80% by mass or less, more preferably 40% by mass or less, and further preferably 20% by mass or less, as a total amount in the sirtuin activators of the present invention.

The drug medicine of the present invention can be administered to humans. Further, the subject to be administered may be animals other than human, that is, there may be mentioned pets such as dog, cat, rabbit, hamster, guinea pig, and squirrel; domestic animals such as cow, horse, and pig; experimental animals such as mouse and rat; animals bred in zoos, or the like.

The sirtuin activator of the present invention can be used as an agent for extending life span or agent for inhibiting aging. β-alanine can act directly on cells to promote the expression of sirtuin genes. It is considered that the promotion of the expression of sirtuin gene can provide the effects of life span extension or senescence inhibition. Furthermore, as shown in the example, β-alanine can promote the expression of sirtuin gene through a substance secreted from muscle cells. It is considered that the promotion of the expression of sirtuin gene may have the effects of extending life span or inhibiting aging. As shown in the example, β-alanine can inhibit the expression of senescence-associated β-galactosidase via a substance secreted from muscle cells. It is considered that the suppression of the expression of senescence-associated β-galactosidase can provide the effects of extending life span or inhibiting aging.

In addition, the sirtuin activator of the present invention can extend life span or inhibit aging via substances secreted from muscle cells (e.g., myokines), as shown in the examples. Etoposide used in the example is an agent that induces cellular senescence by inducing DNA double-strand breaks. Treatment with etoposide increases the activity of senescence-associated β-galactosidase (SA-β-Gal), which is widely used as a marker of cellular senescence. The sirtuin activator of the present invention can decrease the activity of senescence-associated β-galactosidase via a substance secreted from muscle cells, and can be used as an agent for extending life span or agent for inhibiting aging.

[2] Composition for Activating Sirtuin

The composition for activating sirtuin comprises the sirtuin activator as an active ingredient. The compositions for activating sirtuin may contain β-alanine or its salts alone, or a combination of two or more.

The composition for activating sirtuin includes, for example, a pharmaceutical composition, cosmetic composition, or food composition.

The food composition for activating sirtuin of the present invention comprises the sirtuin activator, as long as it can be administered orally. That is to say, the food composition for activating sirtuin of the present invention is possible to use the conditions and the like described in the section of the sirtuin activator, and the same effect can be obtained.

The food in the food composition for activating sirtuin of the present invention is a food or drink, and includes a beverage. The food in the present invention is not particularly limited, for example, there may be mentioned seasonings such as miso, soy sauce, sauce for noodles, sauce, soup stock, pasta sauce, dressing, mayonnaise, tomato ketchup, Worcestershire sauce, sauce for pork cutlet, or sprinkle; instant cooked foods such as a soup base, curry roux, white sauce, rice with tea base, or soup base; soups such as miso soup, soup, consomme soup, or potage soup; processed livestock products such as grilled meat, ham, or sausage; processed marine products such as boiled fish paste, dried fish, salted fish guts, fish boiled in soy sauce, rare delicacy; processed vegetable products such as pickles; snacks such as potato chips, or rice cracker; bakery foods such as bread, sweet bread, or cookies; cooked foods such as boiled foods, fried foods, grilled foods, curry, stew, gratin, rice, porridge, or rice ball; noodles such as pasta, wheat noodle, or ramen; fat processed foods such as margarine, shortening, fat spread, or flavored fat spread; materials for confectionery and bread such as flower pastes, or bean paste; mixed powders such as bread mix powder, cake mix powder, or fried food mix powder; confectioneries such as chocolate, candy, jelly, ice cream, or gum; Japanese confectioneries such as steamed bun, or castella; beverages such as coffee, coffee milk, tea, milk tea, soy milk, nutritional drink, vegetable drink, vinegared drink, juice, cola, mineral water, or sports drink; alcoholic beverages such as beer, wine, cocktail, or sour; milk and dairy products such as bovine milk, yogurt, or cheese.

The food composition for activating sirtuin of the present invention can be prepared by using the known methods for manufacturing foods and drinks except for comprising β-alanine.

The food composition for activating sirtuin of the present invention exhibits the effect same as the sirtuin activator.

The food composition for activating sirtuin of the present invention can be used as an agent for extending life span or agent for inhibiting aging. That is, in this invention, β-alanine was found to have new applications in life span extension or inhibition of aging.

[3] Method for Activating Sirtuin

The method for activating sirtuin of the present invention comprises a step of letting an effective amount of the sirtuin activator of the present invention or the composition for activating sirtuin of the present invention ingest a subject. Therefore, in the sirtuin activation method of the present invention, the "β-alanine", "sirtuin" and the like are the same as those described in the section "[1] Sirtuin activator" of the present invention. The method for activating sirtuin of the present invention exhibits the same effects as those of the sirtuin activator described above. The method for activating sirtuin of the present invention excludes medical treatment for humans. Therefore, sirtuins are activated by application of cosmetic compositions to humans, or by ingestion of food compositions.

[4] Muscle Cell Activator

The muscle cell activator of the present invention comprises β-alanine or salt thereof.

Muscle cells on which the muscle cell activator of the present invention acts, are not particularly limited, include skeletal muscle cells, smooth muscle cells, or cardiac muscle cells.

The muscle cell activation is not particularly limited, but includes, for example, a promotion of myokine secretion from muscle cells. Myokines in the present invention are not limited, as long as their secretion is promoted by β-alanine, but include, for example, IL-6, IL-15, myostatin (GDF-8), IGF, or BDNF. Myokines preferably activate sirtuins or inhibit aging without limitation. In addition, a substance inhibiting aging are, without limitation, a substance that decrease the activity of senescence-associated β-galactosidase.

In the present invention, β-alanine is found to have a new use of promoting the activation of muscle cells. In other words, the present inventors have found that β-alanine can be used as an active ingredient in compositions for activating muscle cells.

EXAMPLES

The present invention will now be further illustrated by, but is by no means limited to, the following Examples.

Example 1

In this example, we measured the transcription of the Sirt1 and Sirt3 genes in β-alanine-treated C2C12 cells, a myoblast cell line derived from mouse skeletal muscle.

First, total RNA in the cells was prepared using the High Pure RNA Isolation Kit (Roche, Basel, Switzerland).

C2C12 cells were seeded in 6-well plates at $4.0\times10^5$ cells/well, and after the cells reached approximately 90% confluency, the culture medium was changed to DMEM medium containing 2% HS to induce differentiation. After that, cells were cultured at 37° C. for about one week in the presence of 5% $CO_2$, while changing the culture medium every 48 hours, and the obtained cells were used for experiments. β-alanine was added to the differentiated cells, and 1×PBS was added to the control cells. Twenty-four hours after the addition of β-alanine, sample was secondary added, and 24 hours after the second addition, the medium was aspirated off and 1 mL/well of 1×PBS was added to wash the cells. Washing was performed twice. Then, 1×PBS (200 μL/well) and Lysis/-binding buffer (400 μL/well) were added to the entire dish, and the total volume was collected in a 1.5-mL tube. The collected samples were suspended using a vortex mixer for 60 seconds. The filter tube and the collection tube were assembled, the sample solution was added to the filter tube, and centrifuged at 4° C., 10000 rpm for 15 seconds. The liquid drained into the collection tube was discarded, and the filter tube and collection tube were assembled again. In a 1.5-mL tube, 90 μL of DNase Incubation Buffer per sample and 10 μL of DNase I per sample were mixed. The mixture was added to the filter tubes and incubated at room temperature for 15 minutes. After incubation, Wash buffer I (500 μL) was added to the filter tubes and centrifuged at 4° C., 10000 rpm for 15 seconds. The liquid drained into the collection tube was discarded, and the filter tube and the collection tube were reassembled. Wash buffer II (500 μL) was added to the filter tube and centrifuged at 4° C., 10000 rpm for 15 seconds. The liquid drained into the collection tube was discarded, and the filter tube and the collection tube were reassembled. Wash buffer II (200 μL) was added to the filter tube and centrifuged at 4° C., 13000×g for 2 minutes. The filter tube was inserted into a new 1.5-mL tube, and Elution buffer (70 μL) was added to the filter tube. The filter tube was left at room temperature for 3 minutes, and centrifuged at 4° C., 10000 rpm for 1 minute. The eluate obtained by the above procedure was used as the RNA solution. The concentration of RNA in the solution was calculated based on the absorbance value at 260 nm using a NanoDrop 2000/2000c spectrophotometer (Thermo Scientific, Waltham, MA, USA) and used in the subsequent experiments.

The cDNA was synthesized as follows. 0.5 μL of Oligo (dT) 20 primer (10 pmoles/μL) was added to 1.0 μg of total RNA extracted from cells, and RNase-free water was added to the total volume to 13.5 μL. The mixture was suspended by tapping, and spun down. Then, it was heat-treated with Thermal Cycler PTC-200 (MJ Research, Waltham, MA, USA) at 65° C. for 5 minutes, immediately transferred to ice and allowed to stand for 5 minutes. 4 μL of 5×RT Buffer (TOYOBO, Osaka, Japan), 2 μL of 10 mM dNTPs (GE Healthcare, Amersham Place, UK), and 0.5 μL of reverse transcription enzyme, ReverTra Ace (100 units/μL) (TOYOBO) were added to 0.2 mL tube per 1 sample, and mixed by pipetting. 6.5 μL of this mixture was added to the tube that was allowed to stand for 5 minutes, and the whole was mixed by pipetting on ice and then spun down.

Then, a cDNA was synthesized by reacting at 42° C. for 20 minutes and 99° C. for 5 minutes, and used as a template for subsequent quantitative real-time PCR.

The quantitative RT-PCR was performed using the prepared cDNA as a template.

49 μL of sterile water, 3.5 μL of each of Primer Forward/Reverse (diluted to 10 μM), 7.0 μL of the template cDNA (diluted to ⅕ for Sirt1 or Sirt3, and diluted to 1/50 for (3-actin) were added to a PCR tube (0.2 mL) on ice. The mixture was spun down, and then 24.5 μL of THUNDERBIRD SYBR qPCR Mix (TOYOBO) was added thereto and the whole was suspended well on ice. As a negative control, 17 μL of sterile water, 0.5 μL of each of Primer Forward/Reverse (diluted to 10 μM) were added to a PCR tube (0.2 mL). The mixture was spun down, and then 7 μL of THUNDERBIRD SYBR qPCR Mix (TOYOBO) was added thereto and the whole was mixed well on ice. Thereafter, 25 μL of the mixture was added to each of 3 wells of a 96-well PCR Plate (NIPPON Genetics, Tokyo, Japan), and quantitative RT-PCR was performed using the Thermal Cycle Dicer Real Time System (Takara, Shiga, Japan). The PCR reaction was performed by 1 cycle of 95° C. for 30 seconds, and 40 cycles of 95° C. for 5 seconds and 60° C. for 60 seconds, and detected by FAM. The expression level of Sirt1 or Sirt3 was relatively quantified by comparing the Ct value of β-actin, which is one of the housekeeping genes, with the Ct value of Sirt1 or Sirt3 using the ΔΔCt method. The synthesis of the primers was outsourced to Sigma, and the sequences of the primers used is as follows.

```
                                     (SEQ ID No: 1)
β-actin forward: 5'-GGCCAGGTCATCACTATTG-3'

                                     (SEQ ID No: 2)
β-actin reverse: 5'-GAGGTCTTTACGGATGTCAAC-3'

                                     (SEQ ID No: 3)
Sirt1 forward: 5'-GCAGACGTGGTAATGTCCAAACAG-3'

                                     (SEQ ID No: 4)
Sirt1 reverse: 5'-ACATCTTGGCAGTATTTGTGGTGAA-3'

                                     (SEQ ID No: 5)
Sirt3 forward: 5'-ATGCACGGTCTGTCGAAGGTC-3'

                                     (SEQ ID No: 6)
Sirt3 reverse: 5'-AGAACACAATGTCGGGTTTCACAA-3'
```

As shown in FIG. 1, the treatment by β-alanine with 500 μM and 1 mM enhanced the expression of Sirt1 and Sirt3 in differentiated C2C12 cells.

Example 2

In this example, a transcription of the Sirt1 gene and Sirt3 gene in HaCaT cells, a human epidermal keratinocyte cell line, was measured.

HaCaT cells were seeded in 6-well plates at $6.0\times10^4$ cells/well. After 24 hours, β-alanine was added to the cells, and 1×PBS was added to the control cells. After 24 hours of the addition, sample was secondary added, and the medium was aspirated after 24 hours of the second addition of sample. Then, 1×PBS was added at 1 mL/well to wash the cells. RNA extraction from cells, cDNA synthesis, and RT-PCR were performed by the same procedure as in Example 1. The sequences of the used primers of the human sirtuin genes are as follows.

```
                                     (SEQ ID No: 7)
Human Sirt1 forward: 5'-GCCTCACATGCAAGCTCTAGTGAC-3'

                                     (SEQ ID No: 8)
Human Sirt1 reverse: 5'-TTCGAGGATCTGTGCCAATCATAA-3'

                                     (SEQ ID No: 9)
Human Sirt3 forward: 5'-AGCCCTCTTCATGTTCCGAAGTGT-3'

                                    (SEQ ID No: 10)
Human Sirt3 reverse: 5'-TCATGTCAACACCTGCAGTCCCTT-3'
```

As shown in FIG. 2, the treatment by β-alanine with 500 μM and 10 mM enhanced the expression of Sirt1 and Sirt3 in the HaCaT cells.

Example 3

In this example, the activation of the sirtuin gene in skin dermal cells via a substance secreted from muscle cells (C2C12 cells) by β-alanine was examined.

C2C12 cells were seeded in 5-mL Dish at $2.0\times10^5$ cells/well, and 48 hours later, the medium was replaced with DMEM medium containing 2% HS to induce differentiation. The culture medium was changed every 2 days to a new medium, and differentiation was induced. Then, the medium was changed every 2 days and β-alanine was added, and the culture supernatant was collected after 8 days of culture. 1×PBS was added to the control cells. After 24 hours of the addition, sample was secondary added, and the culture supernatant was collected after 24 hours of the second addition of sample.

The obtained culture supernatant was added to skin dermal cells (skin dermal fibroblasts) to examine the expression of the sirtuin gene in skin dermal cells. Specifically, cells were seeded at a concentration of $3.0\times10^4$ cells/mL in a 5 mL dish. The culture supernatant of skin fibroblast cells after 24 hours culture was removed, and 5.0 mL/dish of the supernatant of C2C12 cells was added. At this time, 0.444 mL/dish of FBS was added to the culture medium to make up 10% of the culture medium together with HS contained in the culture supernatant of C2C12 cells.

RNA extraction from cells, cDNA synthesis, and RT-PCR were performed by the same procedure as in Example 2. The sequences of the used primers of the human sirt6 gene are as follows. Further, cDNA synthesis was performed using SuperScript IV VILO Master Mix with ezDNase Enzyme, and expression analysis was performed by RT-qPCR using THUNDERBIRD SYBR qPCR Mix.

```
                                    (SEQ ID No: 11)
Human Sirt6 forward: 5'-AATTACGCGGCGGGGCT-3'

                                    (SEQ ID No: 12)
Human Sirt6 reverse: 5'-CGCGCGCTCTCAAAGGT-3'
```

As shown in FIG. 3, a substance secreted by muscle cells (C2C12 cells) enhanced the expression of Sirt1, Sirt3, and Sirt6 in skin dermal cells

Example 4

In this example, the effect on the expression of a senescence marker (senescence-associated β-galactosidase) in skin dermal cells (skin dermal fibroblasts) via a substance secreted from muscle cells by β-alanine was examined.

The procedure in Example 3 was repeated, and the culture supernatant of C2C12 cells was collected. The obtained culture supernatant was added to skin dermal cells (skin dermal fibroblasts) to examine the expression of senescence-associated (β-galactosidase (SA-(β-Gal) in skin dermal cells. The induction of senescence of skin dermal cells was performed as follows using etoposide.

Dermal fibroblasts were seeded onto μClear Fluorescence Black Plates at a concentration of $1.0\times10^5$ cells/mL, and cultured for 24 hours. Then etoposide (FUJIFILM Wako) dissolved in DMSO was added thereto at a final concentration of 50 μM and the whole were incubated at 37° C. for 30 minutes. For the control, dermal fibroblasts were seeded at a concentration of $5.0\times10^4$ cells/mL, and cultured for 24 hours. Then, DMSO of equal volume to that of etoposide was added, and the whole were incubated at 37° C. for 30 minutes.

The culture supernatant of C2C12 cells with β-alanine was obtained in the same procedure as in Example 3.

After culturing the cells for 30 minutes with etoposide, the culture supernatant of skin dermal fibroblasts was removed, and 50 μL/well of the recovered culture supernatant of C2C12 cells was added. In addition, DMEM, 41 μL/well, and FBS 9 μL/well were also added at the same time. After 48 hours of incubation, 100 μL/well of cell fixative solution was added to the cell culture medium and the whole were incubated at room temperature for 10 minutes. The cell culture medium and the cell fixative solution were removed together, and the cells were washed twice with PBS (pH 6.0). Then, 50 μL/well of C12FDG solution was added and the whole was allowed to stand for 10 minutes at room temperature in the dark. After the C12FDG solution was removed, and 50 μL/well of nuclear staining solution was added. Then, the whole was allowed to stand for 30 minutes at room temperature in the dark. After the nuclear staining solution was removed, 100 μL/well of PBS (pH 6.0) was added, and images were acquired by IN Cell Analyzer 2200. The images were analyzed by IN Cell Investigator High-content image analysis software, and the activity of SA-β-Gal was investigated based on the fluorescence intensity of C12FDG. C12FDG is hydrolyzed intracellularly by SA-β-Gal and emits fluorescence. The protocol "HaCaT-eGFP 20190627" was used.

As shown in FIG. 4, the fluorescence intensity of C12FDG, which was significantly enhanced by treatment with etoposide, was decreased by the muscle-mediated action of β-alanine. That is to say, the substance secreted from muscle cells (C2C12 cells) by β-alanine suppressed the expression of SA-β-Gal in dermal skin cells and inhibited the aging of dermal skin cells.

INDUSTRIAL APPLICABILITY

The sirtuin activator and composition for activating sirtuin of the present invention activate sirtuins and can be effectively used to extend life span or inhibit aging.

The invention claimed is:

1. A method of activating sirtuin, comprising administering to a subject in need thereof an effective amount of β-alanine or a salt thereof, such that sirtuin is activated in said subject, wherein said method excludes medical treatment of a human subject.

2. A method of extending life span, or inhibiting aging, or treating a disease, comprising: administering to a subject in need thereof a therapeutically effective amount of β-alanine or a salt thereof, thereby extending the subject's life span, or inhibiting aging in the subject, or treating a disease of the subject.

3. The method of claim 2, wherein the disease is chosen from metabolic disease, neurological disease, cardiovascular disease, chronic obstructive pulmonary disease, osteoporosis, immune disease, and disuse atrophy.

4. The method of activating sirtuin according to claim 1, wherein the sirtuin is that of epidermal keratinocyte cells.

5. The method of activating sirtuin according to claim 1, wherein β-alanine or a salt thereof acts on skeletal muscle cells, and a substance secreted by the skeletal muscle cells activates sirtuin.

6. The method of extending life span or inhibiting aging according to claim 2, wherein β-alanine or a salt thereof acts on skeletal muscle cells, and a substance secreted by the skeletal muscle cells suppresses β-galactosidase (SA-β-Gal) in skin dermal cells.

7. The method of treating a disease according to claim 3, wherein the metabolic disease is metabolic syndrome.

8. The method of treating a disease according to claim 3, wherein the neurological disease is Alzheimer's disease or amyotrophic lateral sclerosis.

9. The method of treating a disease according to claim 3, wherein the cardiovascular disease is arteriosclerosis.

10. The method of treating a disease according to claim 3, wherein the immune disease is atopic dermatitis, hay fever, or rheumatoid arthritis.

11. A method comprising administering to a subject in need thereof an effective amount of a substance secreted from skeletal muscle cells by β-alanine or a salt thereof, thereby (i) activating sirtuin in a subject, wherein activating sirtuin excludes medical treatment of a human subject, (ii) extending the subject's lifespan, or (iii) inhibiting aging in the subject.

* * * * *